United States Patent [19]

Guhl et al.

[11] Patent Number: 4,942,041
[45] Date of Patent: Jul. 17, 1990

[54] PHARMACEUTICAL COMPOSITIONS EFFECTIVE FOR TREATING SKIN TO DESTROY EGGS OF ENTEROBIUS VERMICULARIS

[75] Inventors: Walter Guhl, Haan; Klaus Bansemir, Langenfeld, both of Fed. Rep. of Germany

[73] Assignee: Henkel Kommanditgesellschaft auf Aktien, Duesseldorf-Holthausen, Fed. Rep. of Germany

[21] Appl. No.: 287,436

[22] Filed: Dec. 20, 1988

[30] Foreign Application Priority Data

Dec. 21, 1987 [DE] Fed. Rep. of Germany ....... 3743374

[51] Int. Cl.$^5$ ................. A61K 31/083; A61K 31/155; A61K 31/045; A61K 31/019
[52] U.S. Cl. ...................................... 424/613; 424/62; 514/634; 514/635; 514/557; 514/529
[58] Field of Search ................ 424/613, 601, 62; 514/482, 634, 635, 529, 557

[56] References Cited

U.S. PATENT DOCUMENTS

| 2,684,924 | 7/1954 | Rose et al. ............................. 167/30 |
| 2,836,533 | 12/1955 | Steifter ................................. 424/613 |
| 2,990,425 | 6/1961 | Senior .................................. 260/501 |
| 3,468,898 | 9/1969 | Cutler et al. ......................... 260/301 |
| 4,022,834 | 5/1977 | Gunderson ...................... 260/564 B |
| 4,053,636 | 10/1977 | Eustis, III et al. .................. 424/326 |
| 4,163,800 | 8/1979 | Wickett et al. ...................... 424/613 |
| 4,198,392 | 4/1980 | Juneja ................................... 424/48 |
| 4,420,484 | 12/1983 | Gorman et al. ..................... 424/326 |

FOREIGN PATENT DOCUMENTS

| 0024031 | 2/1981 | European Pat. Off. . |
| 2212259 | 10/1972 | Fed. Rep. of Germany . |
| 2437844 | 6/1975 | Fed. Rep. of Germany . |
| 2627548 | 1/1977 | Fed. Rep. of Germany . |
| 2282262 | 8/1975 | France . |
| 0702268 | 1/1954 | United Kingdom . |
| 1152243 | 5/1969 | United Kingdom . |
| 1344042 | 1/1974 | United Kingdom . |
| 1434040 | 4/1976 | United Kingdom . |
| 1503499 | 3/1978 | United Kingdom . |

OTHER PUBLICATIONS

The New Encyclopaedia Britannica, vol. 9, 15th Edition.

*Primary Examiner*—Anton H. Sutto
*Assistant Examiner*—Edward Rosfjord
*Attorney, Agent, or Firm*—Ernest G. Szoke; Wayne C. Jaeschke; Norvell E. Wisdom, Jr.

[57] ABSTRACT

The use of compositions containing bis- or oligo-bis-guanides, alcohols, hydrogen peroxide, carboxylic acids, and water, applied externally, provides for the effective control of eggs of the threadworm *Enterobius vermicularis* on the skin.

19 Claims, No Drawings

PHARMACEUTICAL COMPOSITIONS EFFECTIVE FOR TREATING SKIN TO DESTROY EGGS OF ENTEROBIUS VERMICULARIS

FIELD OF THE INVENTION

This invention relates to the use of compositions containing biguanido groups, suitable for external application on human skin against eggs of the organism *Enterobius vermicularis*. This organism is variously known under the common names pinworm, seat worm, and threadworm. In this specification, "threadworm" will be used to mean only the same organism as *Enterobius vermicularis*.

STATEMENT OF RELATED ART

Worldwide, around 50% of all human beings are believed to be carriers of parasitic threadworms *Enterobius vermicularis*, also known as oxyurids. This parasitosis occurs commonly in Central Europe, particularly in small children.

Threadworm infestation can spread in two ways: inhalation of infectious embryonized eggs in air or dust (generally relatively mild primary infection) and ingestion of eggs brought directly into the mouth via the hands from scratching in the anal region (massive reinfection). The proliferation cycle of the oxyurids plays a key part so far as reinfection is concerned. After the primary infection and initial colonization in the intestine, the female oxyurids lay their eggs in the anal region during sleep at night so that the eggs are taken up orally either by hand contact from the anal skin to the mouth or aerogenically. Up to 1200 eggs may be found per $cm^2$ of infected anal skin, and often the eggs cannot be completely removed by washing with soap solution. The eggs are also likely to be spread to other members of a family via face cloths and hand to skin contact.

Bis- or oligobisguanides have been taught as disinfecting compounds, cf. British Patent Nos. 702,286 and 1,152,243; German Offenlegungsschriften 2 437 844 (believed to correspond to British Patent No. 1,434,040), 2 212 259 (believed to correspond to British Patent No. 1,344,042), and 2 627 548 (believed to correspond to U.S. Pat. No. 4,198,392); published European Patent Application No. 00 24 031 (believed to correspond to U.S. Pat. No. 4,420,484); and U.S. Pat. Nos. 2,684,924, 2,990,425, 3,468,898, 4,022,834, and 4,053,636. One of the most well-known representatives of these compounds is 1,6-bis-($N^5$-p-chlorophenyl-$N^1$-biguanido)-hexane which is used, in the form of its gluconate in aqueous/alcoholic solutions, in disinfectants under the International Non-Proprietary Name of chlorhexidine. However, these compositions as taught in the references are not suitable for applying to human skin to destroy the eggs of oxyurids.

DESCRIPTION OF THE INVENTION

Except in the operating examples or where otherwise explicitly indicated, all numerical quantities in this description representing amounts of ingredients or reaction or application conditions are to be understood as modified by the word "about".

It has now surprisingly been found that combinations of alcohols, carboxylic acids, peroxides or peroxide releasers, and certain compounds containing at least two biguanido groups (denoted herein as bis- or oligo-bis-guanides), when applied to the skin, destroy the eggs of *Enterobius vermicularis* within a few minutes after application. This form of treatment should preferably be accompanied by internal worm therapy using a conventional anti-worm medication.

Suitable bis- or oligobisguanides for the invention include the compounds with at least two biguanido groups mentioned as suitable for disinfectant compositions in the prior publications cited above. Preferably, the guanides for this invention are selected from the group consisting of:

1,2-bis-($N^5$-p-chlorophenyl-$N^1$-biguanido)-ethane,
1,2-bis-($N^5$-p-nitrophenyl-$N^1$-biguanido)-ethane,
1,2-bis-($N^5$-p-hydroxyphenyl-$N^1$-biguanido)-ethane,
1,2-bis-($N^5$-p-chlorobenzyl-$N^1$-biguanido)-ethane,
1,2-bis-($N^5$-p-bromophenyl-$N^5$-hexyl-$N^1$-biguanido)-ethane,
1,2-bis-($N^5$-p-chlorophenyl-$N^5$-2-ethylphenyl-$N^1$-biguanido)ethane,
1,2-bis-($N^5$-p-chlorophenyl-$N^1$-ethyl-$N^1$-biguanido)-ethane,
1,2-bis-($N^5$-p-methoxyphenyl-$N^1$-biguanido)-ethane,
1,2-bis-($N^5$-p-methylphenyl-$N^1$-biguanido)-ethane,
1,2-bis-($N^5$-3,5-dimethylphenyl-$N^1$-biguanido)-ethane,
1,2-bis-($N^5$-2,6-dichlorophenyl-$N^1$-biguanido)-ethane,
1,2-bis-($N^5$-2,6-dimethylphenyl-$N^1$-biguanido)-ethane,
1,4-bis-($N^5$-p-chlorophenyl-$N^1$-biguanido)-butane,
bis-($N^5$-p-chlorophenyl-$N^1$-biguanido)-methane,
1,3-bis-($N^5$-p-chlorophenyl-$N^1$-biguanido)-propane,
1,6-bis-($N^5$-p-chlorophenyl-$N^1$-biguanido)-hexane,
oligo-bis-guanides as taught in British Patent No. 702,268 and having formulas including the structure

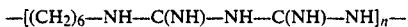

$$-[(CH_2)_6-NH-C(NH)-NH-C(NH)-NH]_n-$$

in which n is an integer not less than 2, preferably from 4 to 6, and pharmaceutically acceptable (non-toxic or irritating) salts of any of the above listed compounds that are sufficiently soluble in water to be compounded in pharmaceutically effective quantities in a water based medication.

Preferable pharmaceutically acceptable salts of the bis- or oligobisguanides to be used in the invention are hydrochlorides, acetates and gluconates; it is particularly preferred to use chlorhexidine gluconate.

Suitable alcohols for use in the invention include any alcohols commonly used in water based pharmaceuticals, preferably those containing from 2 to 8 carbon atoms. Particularly preferred alcohols are ethanol, 1-propanol and 2-propanol, which may be used individually or as mixtures with one another and/or with benzyl alcohol.

The composition in accordance with the invention contains as a further active component hydrogen peroxide or one or more compounds which release hydrogen peroxide when in contact with water, such as peracetic acid.

The compositions in accordance with the invention contain one or more carboxylic acids as another essential active component. Suitable, non-limiting pharmaceutically acceptable carboxylic acids are formic acid, acetic acid, propionic acid, fumaric acid, lactic acid, tartaric acid, 9-undecylenic acid, sorbic acid, and benzoic acid, which may be used individually or in admixture. It is most preferred to use lactic acid.

The compositions in accordance with the invention also contain water in a quantity suitable for the particular formulation. They are preferably formulated as aqueous-alcoholic solutions, although they may also be formulated as film-forming preparations, ointments, emulsions or the like.

Preferably, the compositions in accordance with invention contain 8 to 25, more preferably 12 to 15%, by weight alcohol(s); 0.2 to 0.7, more preferably, 0.3 to 0.6% by weight hydrogen peroxide (or a stoichiometrically equivalent amount of a material that yields hydrogen peroxide by reaction with water); 0.1 to 0.5, more preferably 0.2 to 0.4%, by weight carboxylic acid(s); and 0.05 to 1, more preferably 0.05 to 0.5%, by weight bis- or oligo-bis-guanides or stoichiometrically equivalent amounts of salt(s) thereof. Optionally, the compositions may also contain conventional quantities of conventional pharmaceutical auxiliaries, such as perfumes, dyes, film-forming agents, emulsifiers, thickeners, ointment bases, and the like. Water preferably makes up the balance of the compositions.

Adducts of at least 35 moles of ethylene oxide with one mole of hydrogenated castor oil, adducts of at least 30 moles of ethylene oxide with one mole of non-hydrogenated castor oil, and the monoester of glycerol with lauric acid have proved to be particularly preferable emulsifiers for the compositions according to this invention. Emulsifiers such as these are commercially available.

Other compounds known per se as disinfectants, for example quaternary ammonium compounds, phenolic compounds and the like, may also be added to the compositions in accordance with this invention. However, it has been found that the synergistic combination of bis- or oligobisguanides, hydrogen peroxide, carboxylic acids, and water is sufficient for effectively destroying the eggs of oxyurids.

The invention is illustrated by the following operating example, which does not limit the invention in any way.

EXAMPLE

A composition for destroying eggs of threadworms Enterobius vermicularis was prepared by mixing the following individual constituents;
10% by weight ethanol
0.2% by weight lactic acid
0.5% by weight hydrogen peroxide
0.3% by weight chlorhexidine gluconate
0.1% by weight ether containing oil
0.1% by weight of an adduct of 40 moles of ethylene oxide with 1 mole of hydrogenated castor oil with the balance water.

The ether containing oil was a mixture of the following components in parts by weight:
91.4% natural peppermint oil containing approx. 90% menthol
4.0% salicylic acid phenyl ester
3.5% anethol
0.6% eugenol
0.5% thymol.

The composition thus obtained could be applied in spray form or by means of a swab to the anal skin of a three-and-a-half year old patient with threadworm eggs present on the skin. The instantly recognizable symptoms produced by the eggs (itching) disappeared almost immediately. After two applications, even those worm eggs situated in the deeper creases of the anal skin were destroyed. After accompanying treatment with a standard anti-helminthic and regular treatment every morning with the composition as described above according to this invention, the patient was free of symptoms within a few days.

What is claimed is:

1. A method of treating human patients infested with Enterobius vermicularis, comprising applying to the skin of such patients an amount, which is effective to kill the eggs of Enterobius vermicularis present on such skin within a few minutes of application thereto, of a composition comprising (i) a bis- or oligo-bis-guanide or a water soluble salt thereof, (ii) an alcohol, (iii) hydrogen peroxide or a compound that releases hydrogen peroxide in contact with water, (iv) a carboxylic acid, and (v) water.

2. A method according to claim 1, wherein the weight percentage of alcohol in said composition is from about 8 to about 25, the stoichiometric equivalent weight percent of hydrogen peroxide in said composition is from about 0.2 to about 0.7, the weight percentage of carboxylic acid in said composition is from about 0.1 to about 0.5, and the stoichiometric equivalent weight percentage of bis- or oligo-bis-guanides in said composition is from about 0.05 to about 1.

3. A method according to claim 2, wherein the bis- or oligo-bis-guanide is selected from the group consisting of 1,2-bis-($N^5$-p-chlorophenyl-$N^1$-biguanido)-ethane, 1,2-bis-($N^5$-p-nitro-phenyl-$N^1$-biguanido)-ethane, 1,2-bis-($N^5$-p-hydroxyphenyl-$N^1$-biguanido)-ethane, 1,2-bis-($N^5$-p-chlorobenzyl-$N^1$-biguanido)-ethane, 1,2-bis-($N^5$-p-bromophenyl-$N^5$-hexyl-$N^1$-biguanido)-ethane, 1,2-bis-($N^5$-p-chlorophenyl-$N^5$-2-ethylphenyl-$N^1$-biguanido)-ethane, 1,2-bis-($N^5$-p-chlorophenyl-$N^1$-ethyl-$N^1$-biguanido)-ethane, 1,2-bis($N^5$-p-methoxyphenyl-$N^1$-biguanido)-ethane, 1,2-bis-($N^5$-p-methylphenyl-$N^1$-biguanido)-ethane, 1,2-bis-($N^5$-3,5-dimethylphenyl-$N^1$-biguanido)-ethane, 1,2-bis-($N^5$-2,6-dichlorophenyl-$N^1$-biguanido)-ethane, 1,2-bis-($N^5$-2,6-dimethylphenyl-$N^1$-biguanido)-ethane, 1,4-bis-($N^5$-p-chlorophenyl-$N^1$-biguanido)-butane, bis-($N^5$-p-chlorophenyl-$N^1$-biguanido)-methane, 1,3-bis-($N^5$-p-chlorophenyl-$N^1$-biguanido)-propane, 1,6-bis-($N^5$-p-chlorophenyl-$N^1$-biguanido)-hexane, oligo-bis-guanides having formulas including a moiety:

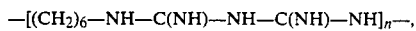

$$-[(CH_2)_6-NH-C(NH)-NH-C(NH)-NH]_n-,$$

in which n is an integer not less than 2, and water-soluble, pharmaceutically acceptable salts of any of these.

4. A method according to claim 3, wherein the carboxylic acid or acids present in the composition are selected from the group consisting of formic acid, acetic acid, propionic acid, fumaric acid, lactic acid, tartaric acid, 9-undecylenic acid, sorbic acid, and benzoic acid.

5. A method according to claim 4, wherein the predominant alcohol or alcohols present in the composition are ethanol, 1-propanol, or 2-propanol.

6. A method according to claim 5, wherein the predominant guanide in the composition is chlorhexidine gluconate.

7. A method according to claim 4, wherein the predominant guanide in the composition is chlorhexidine gluconate.

8. A method according to claim 3, wherein the predominant guanide in the composition is chlorhexidine gluconate.

9. A method according to claim 2, wherein the predominant guanide in the composition is chlorhexidine gluconate.

10. A method according to claim 1, wherein the predominant guanide in the composition is chlorhexidine gluconate.

11. A method according to claim 10, wherein the carboxylic acid present in the composition is predominantly lactic acid.

12. A method according to claim 9, wherein the carboxylic acid present in the composition is predominantly lactic acid.

13. A method according to claim 8, wherein the carboxylic acid present in the composition is predominantly lactic acid.

14. A method according to claim 7, wherein the carboxylic acid present in the composition is predominantly lactic acid.

15. A method according to claim 6, wherein the carboxylic acid present in the composition is predominantly lactic acid.

16. A method according to claim 5, wherein the alcohol in the composition is predominantly ethanol.

17. A method according to claim 4, wherein the alcohol in the composition is predominantly ethanol.

18. A method according to claim 3, wherein the alcohol in the composition is predominantly ethanol.

19. A method according to claim 12, wherein the alcohol in the composition is predominantly ethanol.

* * * * *